US008129112B2

(12) United States Patent
Raimundo et al.

(10) Patent No.: US 8,129,112 B2
(45) Date of Patent: Mar. 6, 2012

(54) POLYMORPHISMS IN THE HUMAN CYP2D6 GENE PROMOTER REGION AND THEIR USE IN DIAGNOSTIC AND THERAPEUTIC APPLICATIONS

(75) Inventors: Sebastian Raimundo, Stuttgart (DE); Ulrich Zanger, Korntal (DE)

(73) Assignee: PGxHealth, LLC, Newton, MA (US)

( * ) Notice: Subject to any disclaimer, the term of this patent is extended or adjusted under 35 U.S.C. 154(b) by 784 days.

(21) Appl. No.: 10/182,977

(22) PCT Filed: Jan. 30, 2001

(86) PCT No.: PCT/EP01/00954
§ 371 (c)(1),
(2), (4) Date: Jan. 24, 2003

(87) PCT Pub. No.: WO01/55432
PCT Pub. Date: Aug. 2, 2001

(65) Prior Publication Data
US 2004/0224424 A1     Nov. 11, 2004

(30) Foreign Application Priority Data

Jan. 31, 2000    (EP) .................................... 00101889

(51) Int. Cl.
*C12Q 1/68*        (2006.01)
*C07H 21/04*       (2006.01)
*C12P 19/34*       (2006.01)
(52) U.S. Cl. ..................... 435/6.1; 536/24.3; 435/91.2
(58) Field of Classification Search ........................ None
See application file for complete search history.

(56) References Cited

FOREIGN PATENT DOCUMENTS
WO    WO 01/96604 A2    6/2001

OTHER PUBLICATIONS

Gaedigk, et al, The Pharmacogenomics Journal (2005) vol. 5, pp. 173-182.*
Zanger, et al, Naunyn-Schmiedeberg's Arch Pharmacology (2004) vol. 369, pp. 23-37.*
Bradford, Pharmacogenomics (2002) vol. 3, pp. 229-243.*
Johnson et al, The Journal of Pharmacology and Experimental Therapeutics (2000) vol. 294 pp. 1099-1105).*
Raimundo et al, Pharmacogenetics (2000) vol. 10, pp. 577-581.*
Ikenaga, et al, Drug metab. Pharmacokinet. (2005) vol. 20, pp. 113-116.*
Lee et al, Clinical Pharmacology and Therapeutics (2004) vol. 75 p. P67.*
Zanger et al., Pharmacogenetics (2001) vol. 11, pp. 573-585.*
Dring, et al, Biochemical Journal (1970) vol. 116, pp. 425-435.*
CYP2D6 allele nomenclature Website (www.cypalleles.ki.se/cyp2d6.htm, pp. 1-9, Aug. 14, 2004).*
GenBank Accession AC008170 GI:5630067 (Jul. 28, 1999, pp. 1-55).*
GenBank Accession NM_000106.1 GI:450322 (Mar. 19, 1999).*
Chee (Wo 1995/11995, published May 4, 1995).*
Johansson, I. et al., "Genetic Analysis of the Chinese Cytochrome P4502D Locus: Characterization of Variant CYP2D6 Genes Present in Subjects with Diminished Capacity for Debrisoquine Hydroxylation," *Molecular Pharmacology*, 46:452-459 (1994).
Cairns, W. et al., "Characterization of the Human Cytochrome P4502D6 Promoter," *The Journal of Biological Chemistry*, 41:25269-25276 (1996).
Daly, A. K. et al., "Recent Advances in Understanding the Molecular Basis of Polymorphisms in Genes Enclosing Cytochrome P450 Enzymes," *Toxicology Letters*, 102-103:143-147 (1998).
Kimura, S. et al., "The Human Debrisoquine 4-Hydroxylase (CYP2D) Locus: Sequence and Identification of the Polymorphic CYP2D6 Gene, a Related Gene, and a Pseudogene," *American Jouran of Human Genetics*, 45:889-904 (1989).
Griese, E. et al., "Assessment of the Predictive Power of Genotypes for the In-vivo Catalytic Function of CYP2D6 in a German Population," *Pharmacogenetics*, 8:15-26 (1998).
Johansson, I. et al., "Inherited Amplification of an Active Gene in the Cytochrome P450 Cyp2d Locus as a Cause of Ultrarapid Metabolism of Debrisoquine," *Proceeding of National Academy of Science USA*, 90:11825-11829 (1993).
Meyer, U. A. et al. "Molecular Mechanisms of Genetic Polymorphisms of Drug Metabolism," *Annual Review of Pharmacological Toxicology*, 37:269-296 (1997).
Wolf, C.R. et al. "Chapter 18. Cytochrome P450 CYP2D6," *ARC Scientific Publications*, 209-221 (1999).
Raimundo, S. et al. "Elucidation of the Genetic Basis of the Common 'Intermediate Metabolizer' Phenotype for Drug Oxidation by CYP2D6," *Pharmacogenetics*, 10:577-581 (2000).
Løvlie, R. et al. "Polymorphisms in CYP2D6 Duplication-negative Individuals with the Ultrarapid Metabolizer Phenotype: A Role for the CYP2D6*35 Allele in Ultrarapid Metabolism?" *Pharmacogenetics*, 11:45-55 (2001).
Zanger, U. M. et al. "Comprehensive Analysis of the Genetic Factors Determining Expression and Function of Hepatic CYP2D6," *Pharmacogenetics*, 11:573-585 (2001).
CYP2D6 Allele Nomenclature, retrieved from internet, Jan. 13, 2002.
Marez, D. et al., "Polymorphism of the Cytochrome P450 CYP2D6 Gene in a European Population: Charactermization of 48 Mutations and 53 Alleles, Their Frequencies and Evolution," *Pharmacogenetics*, 7, 3:193-202 (1997). Lundqvist, E. et al., "Genetic mechanisms for duplication and multiduplication of the human CYP2D6 gene and methods for detection of duplicated CYP2D6 genes," Gene, 226:327-338 (1999).
"Association for Medical School Pharmacology—Knowledge Objectives," http://www.aspet.org/AMSPC/Knowledge_Objectives/files/2-General-Principles.htm.
"Pharmacometric Resources," http://health.auckland.ac.nz/pharmacology/staff/nholford/pkpd/pkpd.htm.

(Continued)

*Primary Examiner* — Steven Pohnert
(74) *Attorney, Agent, or Firm* — McCarter & English, LLP (57) ABSTRACT

Provided are polynucleotides of molecular variant promoters of the CYP2D6 gene which, for example, are associated with abnormal drug response or individual predisposition to several common diseases and disorders caused by drug under- or over-metabolization, and vectors comprising such polynucleotides. Furthermore, methods of diagnosing the status of disorders related to intermediate metabolization of drugs are described. In addition, kits comprising oligonucleotides hybridizing to the CYP2D6 promoter and/or being capable of being extended into this region useful for diagnosing subjects that are ultrarapid or intermediate metabolizer of drugs are provided.

10 Claims, 5 Drawing Sheets

OTHER PUBLICATIONS

Wikipedia, the free encyclopedia. "Pharmacodynamics", modified Jun. 2005.

Zanger et al. "Polymorphic Cytochromes P450 *CYP2B6* and *CYP2D6*: Recent Advances on Single Nucleotide Polymorphisms Affecting Splicing", *ACTA Chim. Slov.* 2008, 55, 38-44.

Chou, Wen-Hwei et al., "Comparison of Two *CYP2D6* Genotyping Methods and Assessment of Genotype-Phenotype Relationships," *Clinical Chemistry*, 49:4 pp. 542-551 (2003).

Johansson, Inger et al., "Inherited amplification of an active gene in the cytochrome P450 *CYP2D* locus as a cause of ultrarapid metabolism of debrisoquine," *CProc. Natl. Acad. Sci. USA*, vol. 90:11825-11829 (1993).

\* cited by examiner

```
-1619  GAATTCAAGA CCAGCCTGGA CAACTTGGAA GAACCSGGTC TCTACAAAAA
                   upfl4==>

-1569  ATACAAAATT AGCTGGGATT GGGTGCGGTG GCTCATGCCT ATAATCCCAG
-1519  CACTTTGGGA GCCTGAGGTG GGTGGATCAC CTGAAGTCAG GAGTTCAAGA
-1469  CTAGCCTGGC CAACATGGTG AAACCCTATC TCTACTGAAA ATAYAAAAAG
-1419  CTAGACGTGG TGGCACACAC CTGTAATCCC AGCTACTTAG GAGGCTGAGG
-1369  CAGGAGAATT GCTTGAAGCC TAGAGGTGAA GGTTGTAGTG AGCCGAGATT
-1319  GCATCATTGC ACAATGGAGG GGAGCCACCA GCCTGGGCAA CAAGAGGAAA
                                                      <==R1
-1269  TCTCCGTCTC CAAAAAAAAA AAAAAAAAAA AAAGRATTAG GCTGGGTGGT

-1219  GCCTGTAGTC CCAGCTACTT GGGAGGCAGG GGGTCCACTT GATGTCGAGA
-1169  CTGCAGTGAG CCATGATCCT GCCACTGCAC TCCGGCCTGG GCAACAGAGT
                                                       <==R2
-1119  GAGACCCTGT CTAAAGAAAA AAAAAATAAA GCAACATATC CTGAACAAAG
-1069  GATCCTCCAT AACGTTCCCA CCAGATTTCT AATCAGAAAC ATGGAGGCCA
                                                f2==>
-1019  GAAAGCAGTG GAGGAGGACR ACCCTCAGGC AGCCCGGGAG GATGTTGTCA
           <==R3
 -969  CAGGCTGGGG CAAGGGCCTT CCGGCTACCA ACTGGGAGCT CTGGGAACAG
 -919  CCCTGTTGCA AACAAGAAGC CATAGCCCGG CCAGAGCCCA GGAATGTGGG
 -869  CTGGGCTGGG AGCAGCCTCT GGACAGGAGT GGTCCCATCC AGGAAACCTC
 -819  CGGCATGGCT GGGAAGTGGG GTACTTGGTC CCGGGTCTGT ATGTGTGTGT
 -769  GACTGGTGTG TGTGAGAGAG AATGTGTGCY CTAAGTGTCA GTGTGAGTCT
 -719  GTGTATGTGT GAATATTGTC TTTGTGTGGG TGATTTTCTR CGTGTGTAAT
 -669  CGTGTCCCTG CAAGTGTGAA CAAGTGGACA AGTGTCTGGG AGTGGACAAG
                                     F3==>
 -619  AGATCTGTGC, ACCATCAGGT GTGTGCATAG CGTCTGTGCA TGTCAAGAGT
 -569  GCAAGGTGAA GTGAAGGGAC CAGGCCCATG ATGCCACTCA TCATCAGGAG
 -519  CTCTAAGGCC CCAGGTAAGT GCCAGTGACA GATAAGGGTG CTGAAGGTCA
                                   <==R4
 -469  CTCTGGAGTG GGCAGGTGGG GGTAGGGAAA GGGCAAGGCC ATGTTCTGGA
 -419  GGAGGGGTTG TGACTACATT AGGGTGTATG AGCCTAGCTG GGAGGTGGAT
 -369  GGCCRGGTCC ACTGAAACCC TGGTTATCCC AGAAGGCTTT GCAGGCTYCA
 -319  GGAGCTTGGA GTGGGAGAG GGGGTGACTT CTCCGACCAG GCCCCTCCAC
 -269  CGGCCTACCC TGGGTAAGGG CCTGGAGCAG GAAGCAGGGG CAAGAACCTC
 -219  TGGAGCAGCC CATACCCGCC CTGGCCTGAC TCTGCCACTG GCAGCACAGT
 -169  CAACACAGCA GGTTCACTCA CAGCAGAGGG CAAAGGCCAT CATCAGCTCC
 -119  CTTTATAAGG GAAGGGTCAC GCGCTCGGTG TGCTGAGAGT GTCCTGCCTG
  -69  GTCCTCTGTG CCTGGTGGGG TGGGGTGCC AGGTGTGTCC AGAGGAGCCC
                   .-1+1
  -19  ATTTGGTAGT GAGGCAGGTA TGGGCTAGA AGCACTGGTG CCCCTGGCCG
                   <==R5                                   <
   32  TGATAGTGGC CATCTTCCT
           =upr1669
```

POLYMORPHISMS IN THE HUMAN CYP2D6 GENE PROMOTER REGION AND THEIR USE IN DIAGNOSTIC AND THERAPEUTIC APPLICATIONS

FIELD OF THE INVENTION

The present invention relates generally to means and methods of diagnosing and treating the phenotypic spectrum as well as the overlapping clinical characteristics with several forms of inherited abnormal expression and/or function of the cytochrome P-450 (CYP)2D6 gene. In particular, the present invention relates to polynucleotides of molecular variant promoters of the CYP2D6 gene which, for example, are associated with abnormal drug response or individual predisposition to several common diseases and disorders caused by drug under- or overmetabolization, and to vectors comprising such polynucleotides. Furthermore, the present invention relates to host cells comprising such polynucleotides or vectors. Moreover, the present invention relates to methods for identifying and obtaining drug candidates for therapy of disorders related to the malfunction of the CYP2D6 gene as well as to methods of diagnosing the status of such disorders. The present invention furthermore provides kits comprising oligonucleotides hybridizing to the CYP2D6 promoter and/or being capable of being extended into this region useful for diagnosing subjects that are for example ultrarapid or intermediate metabolizer of drugs.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

Cytochrome P450 CYP2D6 belongs to the CYP2 family of P450s and is the only functionally active isozyme of the CYP2D subfamily in humans. It is involved in the metabolism of up to 25% of all therapeutically used drugs (Hardman et al, 1995). The gene encoding its synthesis is located in the CYP2D locus at q13.1 on the long arm of chromosome 22 (Eichelbaum et al., 1987). It is part of a gene cluster containing also two pseudogenes CYP2D7P and CYP2D8P (Kimura et al., 1989). Like other members of the human CYP2 gene family, the CYP2D genes consist of 9 exons and 8 introns. The enzyme exhibits a common genetic polymorphism (Meyer and Zanger, 1997). In fact it was the first cytochrome P450 enzyme for which a genetic polymorphism was demonstrated which was named the debrisoquine/sparteine polymorphism based on the two substrates involved in its discovery (Mahgoub et al., 1977; Eichelbaum et al., 1979). Depending on the metabolic handling of these two probe drugs, between 5 and 10% of subjects of European populations have a severely impaired capacity to form the major metabolites 4-hydroxydebrisoquine and 2-dehydrosparteine. These subjects were designated as poor metabolizers (PM), the remainder of the population being so-called extensive metabolizers (EM). The trait 'poor metabolism' is inherited in an autosomal recessive fashion, i.e. PMs are carriers of two non-functional alleles. The molecular basis of this polymorphism has been extensively investigated and more than 30 functional and non-functional alleles have been described which allow to predict the PM phenotype in Caucasians with an estimated 99% reliability. (Daly et al., 1996 and CYP Allele Nomenclature Web-Site: http://www.imm.ki.se/CYP-alleles/cyp2d6.htm).

Over 50-fold variability in CYP2D6 activity exists among extensive metabolizers (genetically carriers of at least one functional allele) which has led to the designation of the most rapid "extensive" phenotype as "ultrarapid" (UM) and the slowest as "intermediate" metabolizer (IM). There is evidence in the literature that these sub-phenotypes are clinically relevant. Individuals with the UM phenotype are at risk to experience therapeutic failure due to abnormally fast clearance of the drug whereas IMs may be comparable to PMs in their risk to develop adverse side effects and toxicity.

A molecular explanation for the UM phenotype was provided by the discovery of the CYP2D6 gene duplication, which however only applies to a fraction of UMs (Johansson et al., 1993; Dahl et al., 1995). Two CYP2D6 alleles previously described result in lower enzyme activity and cause the IM phenotype in individuals not carrying a normal functional allele. However, both of these alleles (*9: Broly and Meyer, 1993; *10: Yokota et al., 1993) occur with a frequency of only 2% in the Caucasian population and only about 20% of the IMs have informative genotypes involving these two alleles (i.e. *9/*0, *10/*0 and *10/*10; Sachse et al., 1997; Griese et al., 1998). 80% of the IMs have therefore "uninformative" genotypes, i.e. genotypes that are also associated with the normal extensive or the ultrarapid metabolizer phenotypes. It has therefore remained unclear whether the IM sub-phenotype has a genetic basis or whether it is an epigenetic phenomenon.

It is clear that naturally occurring mutations, if they exist can have effects on drug metabolization and efficacy of therapies with drugs. It is unknown, however, how many of such variations exist, and with what frequency and at what positions in the human CYP2D6 genes.

Accordingly, means and methods for diagnosing and treating a variety of forms of individual drug intolerability and inefficacy of drug therapy which result from CYP2D6 gene polymorphisms that interfere e.g., with chemotherapeutic treatment of diseases was hitherto not sufficiently available but are nevertheless highly desirable.

Thus, the technical problem of the present invention is to comply with the needs described above.

The solution to this technical problem is achieved by providing the embodiments characterized in the claims.

SUMMARY OF THE INVENTION

The present invention is based on the finding of novel, so far unknown variations in the nucleotide sequences of the CYP2D6 gene promoter and the population distribution of these alleles. Based upon the knowledge of these novel sequences diagnostic tests and reagents for such tests were designed for the specific detection and genotyping of CYP2D6 promoter alleles in humans, including homozygous as well as heterozygous, frequent as well as rare alleles of the CYP2D6 promoter. The determination of the CYP2D6 promoter allele status of humans with such tests is useful for the optimization of therapies with the numerous substrates of CYP2D6.

In a first embodiment, the invention provides polynucleotides of molecular variant CYP2D6 gene promoter and embodiments related thereto such as vectors and host cells transferred therewith.

In yet another embodiment, the invention provides methods for therapy of disorders related to acquired drug hypo- or hypersensitivity as well as methods of diagnosing the status of such disorders.

In a further embodiment, the invention provides kits comprising the above-described polynucleotides or vectors containing the same.

The novel variant forms of CYP2D6 gene according to the invention provide the potential for the development of a pharmacodynamic profile of drugs for a given patient.

DESCRIPTION OF THE INVENTION

The finding and characterization of variations in the CYP2D6 genes, and diagnostic tests for the discrimination of different CYP2D6 alleles in human individuals provide a very potent tool for improving the therapy of diseases with drugs that are targets of the CYP2D6 gene product, and whose metabolization is therefore dependent on CYP2D6 activity. The diagnosis of the individual allelic CYP2D6 status permits a more focused therapy, e.g., by opening the possibility to apply individual dose regimens of drugs. It may also be useful as prognostic tool for therapy outcome. Furthermore, diagnostic tests to genotype CYP2D6 will improve therapy with established drugs and help to correlate genotypes with drug activity or side effects.

Thus, the present invention provides a way to exploit molecular biology and pharmacological research for drug therapy while bypassing their potential detrimental effects which are due to expression of variant expression of the CYP2D6 gene.

Accordingly, the invention relates to a polynucleotide selected from the group consisting of:
(a) a molecular variant polynucleotide having the nucleic acid sequence of SEQ ID NO: 1, wherein at nucleotide position corresponding to nucleotide position −1584 of the CYP2D6 promotor as shown in FIG. 1, is a G;
(b) a molecular variant polynucleotide capable of hybridizing to the CYP2D6 promoter as shown in FIG. 1, wherein said polynucleotide is having at a position corresponding to position −1584 of the CYP2D6 promoter as shown in FIG. 1 at least one nucleotide deletion, addition and/or substitution; and
(c) a molecular variant polynucleotide capable of hybridizing to the CYP2D6 promoter as shown in FIG. 1, wherein said polynucleotide is having at a position corresponding to position −1584 of the CYP2D6 promoter as shown in FIG. 1, a G.

In the context of the present invention the term "molecular variant" CYP2D6 promoter, gene or protein as used herein means that said CYP2D6 promoter, gene or protein differs from the wild type CYP2D6 promoter, gene or protein by way of nucleotide substitution(s), addition(s) and/or deletion(s) (Genomic sequences of the CYP2D6 gene including the promoter are described, for example, in Genbank.

The term "corresponding" as used herein means that a position is not only determined by the number of the preceding nucleotides. The position of a given nucleotide in accordance with the present invention which may be deleted, substituted or comprise one or more additional nucleotide(s) may vary due to deletions or additional nucleotides elsewhere in the promotor or gene. Thus, under a "corresponding position" in accordance with the present invention it is to be understood that nucleotides may differ in the indicated number but may still have similar neighboring nucleotides. Said nucleotides which may be exchanged, deleted or comprise additional nucleotides are also comprised by the term "corresponding position". Said nucleotides may for instance together with their neighbors form sequences which may be involved in the regulation of gene expression, stability of the corresponding RNA or RNA editing.

The term "hybridizing" as used herein refers to polynucleotides which are capable of hybridizing to the polynucleotides of the invention or parts thereof which are associated with altered expression of the variant CYP2D6 gene compared to the corresponding wild type gene. Thus, said hybridizing polynucleotides are also associated with said altered expression of the variant CYP2D6 gene compared to the corresponding wild type gene. Therefore, said polynucleotides may be useful as probes in Northern or Southern Blot analysis of RNA or DNA preparations, respectively, or can be used as oligonucleotide primers in PCR analysis dependent on their respective size. Also comprised by the invention are hybridizing polynucleotides which are useful for analysing DNA-Protein interactions via, e.g., electrophoretic mobility shift analysis (EMSA). Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Molecular Cloning A Laboratory Manual, Cold Spring Harbor Laboratory (1989) N.Y. Preferred in accordance with the present inventions are polynucleotides which are capable of hybridizing to the polynucleotides of the invention or parts thereof which are associated with altered expression of the variant CYP2D6 gene compared to the corresponding wild type gene under stringent hybridization conditions, i.e. which do not cross hybridize to unrelated polynucleotides such as polynucleotides that may not alter expression of the variant CYP2D6 gene compared to the corresponding wild type gene.

In accordance with the present invention, the mode and population distribution of novel so far unidentified genetic variations in the CYP2D6 gene have been analyzed by sequence analysis of relevant regions of the human CYP2D6 genes from many different individuals. It is a well known fact that genomic DNA of individuals, which harbor the individual genetic makeup of all genes, including CYP2D6 can easily be purified from individual blood samples. These individual DNA samples are then used for the analysis of the sequence composition of the CYP2D6 gene alleles that are present in the individual which provided the blood sample. All previously reported studies on the CYP2D6 polymorphism were restricted and focused to the coding sequence which comprises 9 exons. This work represents the first systematic mutation analysis of the promoter region of the gene. The aim was to identify mutations, if any that are linked to altered enzyme activity in vivo, based on the assumption that promoter mutations may affect gene transcription which may result in higher or lower mRNA levels and thus lead to higher or lower amounts of enzyme expressed in liver. Surprisingly, mutations in the CYP2D6 promoter could be found that are associated with enhanced and reduced CYP2D6 enzyme activity, respectively. The sequence analysis was carried out by PCR amplification of relevant regions of the CYP2D6 gene, subsequent purification of the PCR products, followed by automated DNA sequencing with established methods; see the examples. In particular a subgroup of 10 to 15% of Caucasians are termed phenotypical "intermediate metabolizers" of drug substrates of CYP2D6, because they have severely impaired yet residual in vivo function of this cytochrome P450. Genotyping based on the currently known CYP2D6 alleles does not predict this phenotype. In accordance with the present invention, a systematic search through 1.6 kb of the CYP2D6 5'-flanking sequence revealed 6 mutations of which three were exclusively associated with the functional CYP2D6*2 allele and one of these co-segregated with increased CYP2D6*2 activity in a family study. In a representative population sample the median urinary metabolic ratio ($MR_S$) for sparteine oxidation was over 4-fold reduced in individuals with the novel variant allele (*2[−1584G]: $MR_S$=0.53, N=27) compared to individuals lacking the mutation (*2[−1584C]: $MR_S$=2.33, N=12; P<0.0001). This first functional promoter variant of the CYP2D6 gene has an estimated frequency of 20% to 25% in the general population and allows to establish a genotype for the identification of over 50% of Caucasians with the intermediate metabolizer phenotype.

One important parameter that had to be considered in the attempt to determine the individual CYP2D6 genotype and identify novel CYP2D6 variants by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel CYP2D6 gene polymorphisms (homozygous and heterozygous) are described in the examples below.

The mutations in the CYP2D6 gene detected in accordance with the present invention are illustrated in FIG. 1 and Table 2, respectively. The methods of the mutation analysis followed standard protocols and are described in detail in the examples. In general such methods to be used in accordance with the present invention for evaluating the phenotypic spectrum as well as the overlapping clinical characteristics with other forms of drug metabolization and altered tolerance to drugs in patients with mutations in the CYP2D6 gene encompass for example haplotype analysis, single-strand conformation polymorphism analysis (SSCA), PCR and direct sequencing. On the basis of thorough clinical characterization of many patients the phenotypes can then be correlated to these mutations as well as to mutations that had been described earlier. As is evident to the person skilled in the art this new molecular genetic knowledge can now be used to exactly characterize the genotype of the index patient where a given drug takes an unusual effect and of his family.

Over the past 20 years, genetic heterogeneity has been increasingly recognized as a significant source of variation in drug response. Many scientific communications (Meyer and Zanger, 1997; West et al., 1997) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's, (Marshall, 1997a and 1997b). In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient. For the providers of health care, such as health maintenance organizations in the US and government public health services in many European countries, this pharmacogenomics approach can represent a way of both improving health care and reducing overheads because there is a large cost to unnecessary therapies, ineffective drugs and drugs with side effects.

In a preferred embodiment, the present invention relates to polynucleotides of molecular variant CYP2D6 gene promoters, wherein the nucleotide deletion, addition and/or substitution result in altered expression of the variant CYP2D6 gene compared to the corresponding wild type gene.

The polynucleotide of the invention may be, e.g., DNA, genomic DNA or synthetically produced DNA or a recombinantly produced chimeric nucleic acid molecule comprising any of those polynucleotides either alone or in combination. Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). The present invention furthermore relates to host cells transformed with a polynucleotide or vector of the invention. Said host cell may be a prokaryotic or eukaryotic cell.

With the variant CYP2D6 polynucleotides and vectors of the invention, it is now possible to study in vivo and in vitro the efficiency of drugs in relation to particular mutations in the CYP2D6 gene of a patient and the affected phenotype. Thus, a particular object of the present invention concerns drug/pro-drug selection and formulation of pharmaceutical compositions for the treatment of diseases which are amenable to chemotherapy taking into account the polymorphism of the variant form of the CYP2D6 gene promoter that cosegregates with the affected phenotype of the patient to be treated. This allows the safe and economic application of drugs which for example were hitherto considered not appropriate for therapy of, e.g., cancer due to either their side effects in some patients and/or their unreliable pharmalogical profile with respect to the same or different phenotype(s) of the disease. The means and methods described herein can be used, for example, to improve dosing recommendations and allows the prescriber to anticipate necessary dose adjustments depending on the considered patient group.

Accordingly, in a further important embodiment the present invention relates to a method of diagnosing a disorder related to reduced or enhanced capacity for clearance of CYP2D6 substrates or susceptibility to such a disorder comprising determining the presence of a mutation in the promoter of the CYP2D6 gene in a sample from a subject.

In accordance with this embodiment of the present invention, the method of testing the status of a disorder or susceptibility to such a disorder can be effected by using a polynucleotide or a nucleic acid molecule of the invention, e.g., in the form of a Southern blot or in situ analysis. Said nucleic acid sequence may hybridize to the promoter or a coding region of the CYP2D6 gene or to a non-coding region, e.g., intron and should be capable of being extended into the CYP2D6 promoter region. Additionally, said testing can be done in conjunction with an actual blocking, e.g., of the transcription of the gene and thus is expected to have therapeutic relevance. Furthermore, a primer or oligonucleotide can also be used for hybridizing to one of the above-mentioned CYP2D6 genes. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence of variant CYP2D6 gene promoters can be monitored by using a primer pair that specifically hybridizes to a region of the gene encompassing the CYP2D6 promoter and by carrying out an amplification reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985. Furthermore, the genomic DNA obtained from the subject may be sequenced to identify mutations which may be characteristic fingerprints of mutations in the CYP2D6 gene promoter. The present invention further comprises methods wherein such a fingerprint may be generated by RFLPs of DNA obtained from the subject, optionally the DNA may be amplified prior to analysis, the methods of which are well known in the art. For example, the sample nucleic acid, e.g., amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

Further modifications of the above-mentioned embodiment of the invention can be easily devised by the person skilled in the art, without any undue experimentation from this disclosure; see, e.g., the examples. In a preferred embodiment of the present invention, the above described methods comprise PCR, ligase chain reaction, restriction digestion, direct sequencing, nucleic acid amplification techniques or hybridization techniques. Diagnostic screening may be performed for polymorphisms that are genetically linked to a phenotypic variant in CYP2D6 activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium. Linkage analysis may be performed alone, or in combination with direct detection of phenotypically evident polymorphisms. The use of microsatellite markers for genotyping is well documented. For examples, see Mansfield et al., Genomics 24 (1994), 225-233; and Ziegle et al., Genomics 14 (1992), 1026-1031. The use of SNPs for genotyping is illustrated in Golevieva, Am, J. Hum. Genet. 59 (1996), 570-578; and in Underhill et al., Proc. Natl. Acad. Sci. USA 93 (1996), 196-200.

In a preferred embodiment of the present invention the substrate for which reduced or enhanced clearance is observed is selected from the group consisting of antiarrhythmics, beta adrenergic receptor antagonists, tricyclic antidepressants, selective serotonin reuptake inhibitors (SSRI), neuroleptics, opiates, anticancer agents, amphetamines. In a further embodiment of the above-described method, a further step comprising administering to the subject a medicament to abolish or alleviate said disorder in accordance with all applications of the method of the invention allows treatment of a given disease before the onset of clinical symptoms due to the phenotype response caused by the CYP2D6 gene. In a preferred embodiment of the method of the invention said medicament are chemotherapeutic agents such as described above.

Furthermore, the present invention relates to a method for the preparation of a pharmaceutical composition comprising the steps of the above-described methods; and formulating a drug or pro-drug in the form suitable for therapeutic application and preventing or ameliorating the disorder of the subject diagnosed in the method of the invention. Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329). In a preferred embodiment of the method of the present invention said drug or prodrug is a derivative of a medicament as defined hereinbefore.

Furthermore, the present invention relates to the use of an oligo- or polynucleotide for the detection of a polynucleotide of the invention and/or for genotyping of corresponding individual CYP2D6 promoter alleles. Preferably, said oligo- or polynucleotide is a polynucleotide of the invention described before. In a particular preferred embodiment said oligonucleotide is about 15 to 50, preferably 20 to 40, more preferably 20 to 30 nucleotides in length and comprises the nucleotide sequence of any one of SEQ ID NOS: 2 to 10 or a complementary sequence.

Hence, in a still further embodiment, the present invention relates to a primer or probe consisting of an oligonucleotide as defined above. In this context, the term "consisting of" means that the nucleotide sequence described above and employed for the primer or probe of the invention does not have any further nucleotide sequences of the CYP2D6 gene immediately adjacent at its 5' and/or 3' end. However, other moieties such as labels, e.g., biotin molecules, histidin flags, antibody fragments, colloidal gold, etc. as well as nucleotide sequences which do not correspond to the CYP2D6 gene may be present in the primer and probes of the present invention. Furthermore, it is also possible to use the above described particular nucleotide sequences and to combine them with other nucleotide sequences derived from the CYP2D6 gene wherein these additional nucleotide sequences are interspersed with moieties other than nucleic acids or wherein the intervening nucleic acid does not correspond to nucleotide sequences of the CYP2D6 gene. Furthermore, it is evident to the person skilled in the art that the oligonucleotide can be modified, for example, by thio-phosphate-backbones and/or base analogs well known in the art (Flanagan, Proc. Natl. Acad. Sci. USA 96 (1999), 3513-8; Witters, Breast Cancer Res. Treat. 53 (1999), 41-50; Hawley, Antisense Nucleic Acid Drug Dev. 9 (1999), 61-9; Peng Ho, Brain Res. Mol. Brain Res. 62 (1998), 1-11; Spiller, Antisense Nucleic Acid Drug Dev. 8 (1998), 281-93; Zhang, J. Pharmacol. Exp. Ther. 278 (1996), 971-9; Shoji, Antimicrob. Agents Chemother. 40 (1996), 1670-5; Crooke, J. Pharmacol. Exp. Ther. 277 (1996), 923-37). In one embodiment of the invention, an array of oligonucleotides are provided, where discrete positions on the array are complementary to one or more of the provided polymorphic sequences, e.g. oligonucleotides of at least 12 nt. frequently 20 nt. or larger, and including the sequence flanking the polymorphic position. Such an array may comprise a series of oligonucleotides, each of which can specifically hybridize to a different polymorphism. For examples of arrays, see Hacia et al., Nature Genetics 14 (1996), 441-447; Lockhart et al., Nature Biotechnol. 14 (1996), 1675-1680; and De Risi et al., Nature Genetics 14 (1996), 457-460.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients at the wrong dose.

Furthermore, the present invention relates to a kit comprising any one of the afore-described polynucleotides, vectors or probes and optionally suitable means for detection and instructions for carrying out a method of the invention.

The kit of the invention may contain further ingredients such as selection markers and components for selective media suitable for the generation of transgenic cells. The kit of the invention may advantageously be used for carrying out a method of the invention and could be, inter alia, employed in a variety of applications, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or diagnostic compositions may be used for methods for detecting expression of a mutant form of CYP2D6 gene in accordance with any one of the above-described methods of the invention, employing, for example, nucleic acid hybridization and/or amplification techniques such as those described herein before and in the examples.

In another embodiment the present invention relates to the use of a drug or prodrug for the preparation of a pharmaceutical composition for the treatment or prevention of a disorder diagnosed by the method described hereinbefore.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further databases and websites including "ncbi," "infobiogen," and "the Friedrich Miescher Institute for Biomedical Research" are known to the person skilled in the art and can also be obtained using known internet search engines, e.g., lycos.com. An overview of patent information in biotechnology and a survey of relevant sources of patent information useful for retrospective searching and for current awareness is given in Berks, TIBTECH 12 (1994), 352-364.

The methods, use and kits of the invention can be used for the diagnosis and treatment of all kinds of diseases hitherto unknown as being related to or dependent on variant CYP2D6 gene promoters. The compositions, methods and uses of the present invention may be desirably employed in humans, although animal treatment is also encompassed by the methods and uses described herein.

BRIEF DESCRIPTION OF THE FIGURES

FIG. 1: Sequence of the CYPD6 Promoter region (SEQ ID NO: 1), location of primers and mutations. Forward (==>)- and reverse (<==) primers underlined. Numbering according to new numbering system with the A of the initiation codon +1 and the base 5' of the ATG being -1 (see "The Home Page of the Human Cytochrome P450 Allele Nomenclature Committee" website, which adheres to the guidelines provided in Shows et al., Cytogenet Cell Genet 46 (1987), 11-281; Daly et al., Pharmacogenetics 6, (1996), 193-201: Antonarakis and the Nomenclature Working Group, Hum Mutat. 11 (1998), 1-3; and den Dunnen and Antonarakis, Hum Genet. 109 (2001), 121-124). 5'-untranslated region bold (according to Kimura et al., 1989). Mutations in bold. IUPAC nomenclature rules:

K=G or T
Y=C or T
R=A or G
S=C or G

A: Pedigree of a family analyzed for CYP2D6 phenotypes, genotypes and the CYP2D6*2 sequence at position −1584 bp.

B: Direct sequencing of genomic PCR fragments of the CYP2D6 5'-flanking region. The paternal and maternal *2-alleles (see part A) were specifically amplified and sequenced around the mutation at −1584 bp. The sequence around position −1584 for the paternal and maternal *2 alleles is shown in the left (SEQ ID NO: 11) and right (SEQ ID NO:12) panels, respectively.

A: Distribution of the sparteine metabolic ratio $MR_S$ in a previously characterized representative population (N=195, Griese et al., 1998). UM, ultrarapid metabolizer (range: $MR_S<0.2$); EM, extensive metabolizer (range: $MR_S<1.2$); IM, intermediate metabolizer (range: $1.2<MR_S<20$); PM, poor metabolizer (range: $MR_S>20$).

B: $MR_S$ Distribution for all 39 individuals of the population shown in A who had the genotype CYP2D6*2/*0. Hatched bars correspond to individuals with variant allele CYP2D6*2[−1584G], black bars to individuals with the *2[−1584C]-allele.

The invention will now be described by reference to the following examples which are merely illustrative and are not to be construed as a limitation of the scope of the present invention.

EXAMPLES

Example 1

Genomic samples, isolated by standard techniques from human blood samples were obtained from healthy volunteers under consideration of all legal, ethical and medical requirement of the local ethics committee. Blood samples from >50 individuals were obtained and processed by ion exchange chromatography methods (Qiagen) to isolate DNA.

1. Description of Methods:

DNA Samples and PCR Conditions:

Leucocyte DNA from Caucasian individuals was isolated from blood samples by standard methods. All individuals included in this study had been previously phenotyped with sparteine and genotyped for the CYP2D6-polymorphism using published methods (Stüven et al., 1996; Griese et al., 1998). To investigate the promoter region of the CYP2D6 gene, genomic DNA was amplified using a pair of primers upf14 and upr1669, designed to specifically amplify a 1656 by fragment which contains almost the entire known 5'-flanking sequence (FIG. 1, Table 1). Aliquots of each PCR product were subjected to agarose gel electrophoresis to ensure proper amplification.

Amplifications were done in a 50 µl volume containing primers (0.4 µM), dNTP (200 µM), ~100 ng of genomic DNA and the Expand High Fidelity Polymerase system (Boehringer Mannheim). Following 2 min heating at 95° C., thermal cycling of 15 s at 95° C., 30 s at 61° C. and 2 min at 72° C. was performed for 33 cycles and 7 min at 72° C. for 1 cycle on a PTC-200 thermal cycler (MJ Research). The *2-allele was also specifically amplified using primer 10B instead of upr1669, which was designed within a *2-specific sequence in intron 1 (Johansson et al. 1993). In this case, amplification resulted in a ~1.9 kb DNA fragment, as expected, from all DNA samples with a *2-genotype.

TABLE 1

| Oligonucleotide primers | | |
|---|---|---|
| primer designation | sequence (5' → 3') | Corresponding SEQ ID NO: |
| amplification primers: | | |
| upf 14 | GCC TGG ACA ACT TG-G AAG AAC C | SEQ ID NO: 2 |

TABLE 1-continued

| Oligonucleotide primers | | |
|---|---|---|
| primer designation | sequence (5' → 3') | Corresponding SEQ ID NO: |
| upr1669 | AGG AAG ATG GCC AC-T ATC AC | SEQ ID NO: 3 |
| sequencing primers: | | |
| F3 | GAA CAA GTG GA-C AAG TGT CTG | SEQ ID NO: 4 |
| R5 | CCA TAC CTG CCT CAC-TAC C | SEQ ID NO: 5 |
| F2 | TTC CCA CCA-GAT TTC TAA TCA G | SEQ ID NO: 5 |
| R4 | CAG CAC CCT TAT CT-G TCA CT | SEQ ID NO: 7 |
| R3 | GTC CTC CTC CAC T-GC TTT C | SEQ ID NO: 8 |
| R2 | TTA GAC AGG GTC T-CA CTC TGT TG | SEQ ID NO: 9 |
| R1 | GAC GGA GAT TTC-CTC TTG TTG C | SEQ ID NO: 10 |

PCR Product Sequencing:

PCR products were directly sequenced using infrared-800 labeled nested primers (MWG Biotech, Ebersberg, Germany) with the Thermo Sequenase fluorescent labelled primer cycle sequencing kit (Amersham Life Sciences, Little Chalfont, England). The nucleotide sequences of the primers are shown in Table 1. Sequencing analysis was performed on an automated DNA sequencer (Licor 4200, MWG Biotech, Ebersberg, Germany) using Base ImagIR data collection and image analysis 4.00 software.

2. Description of Results:

A total of 8 mutations were detected in the upstream region of the CYP2D6 gene (Table 2).

TABLE 2

Single nucleotide polymorphisms (SNP) in the CYP2D6 promoter

| SNP[1] | mutant alleles[2] | N[3] | frequency[4] | function |
|---|---|---|---|---|
| −1584 C → G | 70% of *2 | >30 | ~20% | increased activity |
| −1426 C → T[5] | *4, *10 | >30 | ~20% | neutral |
| −1235 A → G[5] | *2, *4, *10 | >30 | ~50% | neutral |
| −1000 G → A[5] | *4, *10 | >30 | ~20% | neutral |
| −740 C → T | *2 | >30 | ~30% | unknown |
| −680 G → A | *2 | >30 | ~30% | unknown |
| −365 G → A | *1 | 1 | rare | unknown |
| −322 T → C | *2 | 1 | rare | unknown |

[1]Base numbering according to the Human Cytochrome P450 (CYP) Allele Nomenclature (wild-type sequence as published by Kimura et al., 1989). Totally more than 60 individuals (genotypes comprising alleles *1, *2, *4, *5, *9, *10) were completely sequenced in their CYP2D6 5'-flanking sequence; a compilation of results is presented.
[2]Alleles with mutated sequence as indicated; alleles not mentioned had wild-type sequence.
[3]Approximate number of alleles observed with mutant sequence.
[4]Estimated frequencies for the whole population.
[5]First described for chinese CYP2D locus (Johansson et al., 1994).

Comparison of their linkage patterns in individuals with different CYP2D6 genotypes revealed that some of these mutations occur in a number of different alleles whereas others seem to be associated rather specifically with one particular known allele (Table 2).

Figure 2:
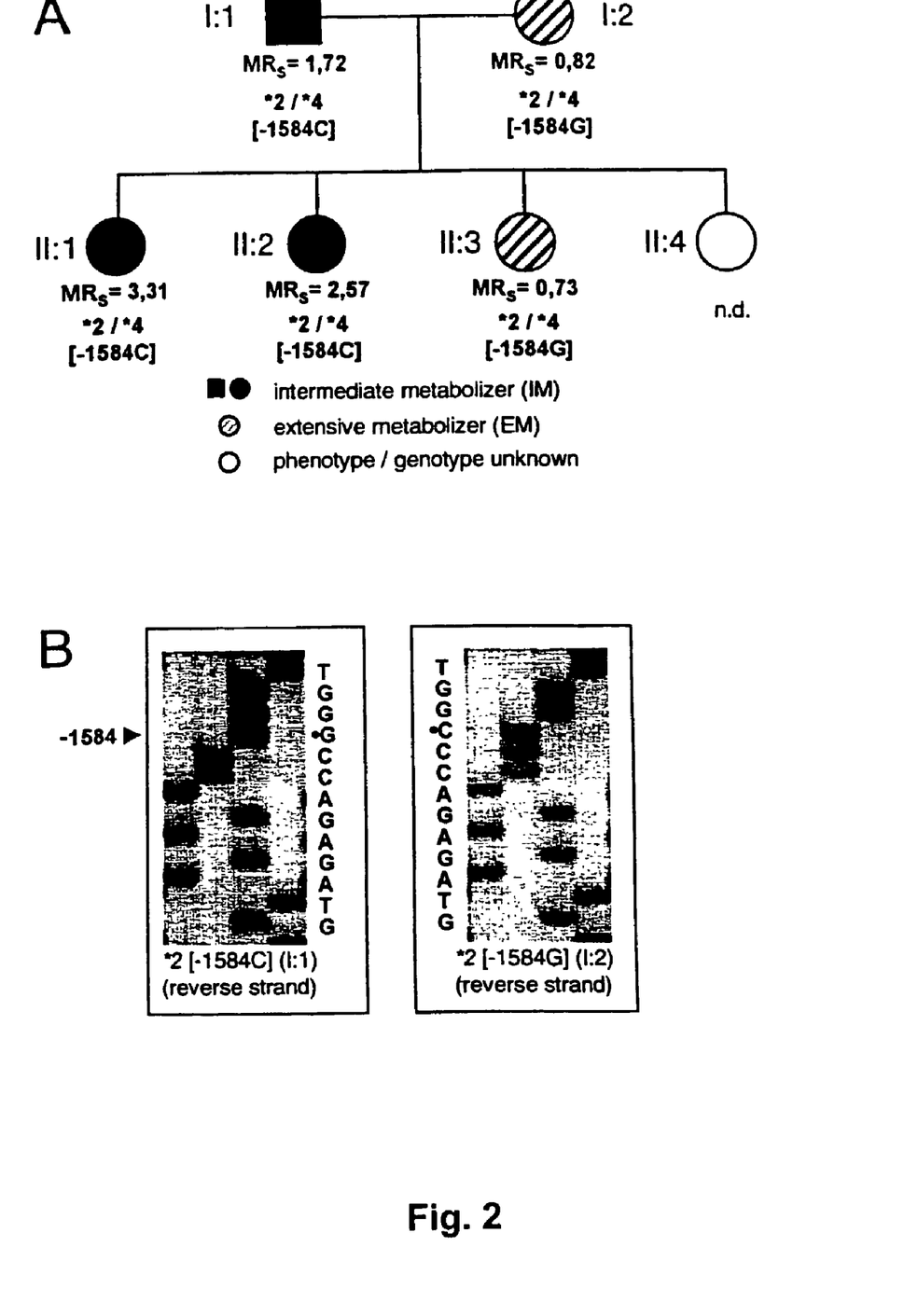
FIG. 2: CYP2D6 phenotype and genotype analysis in a family.

A novel C to G mutation found in 70% of the sequenced *2 alleles at −1584 bp relative to the initiation codon (FIG. 1) was found to be strongly associated with lower metabolic ratios (i.e. higher enzyme activity in vivo). In a family analysis, it could be shown that the [−1584G] allele segregates with low $MR_S$ values whereas the [−1584C] allele segregates with high $MR_S$ values (FIG. 2).

Figure 3:
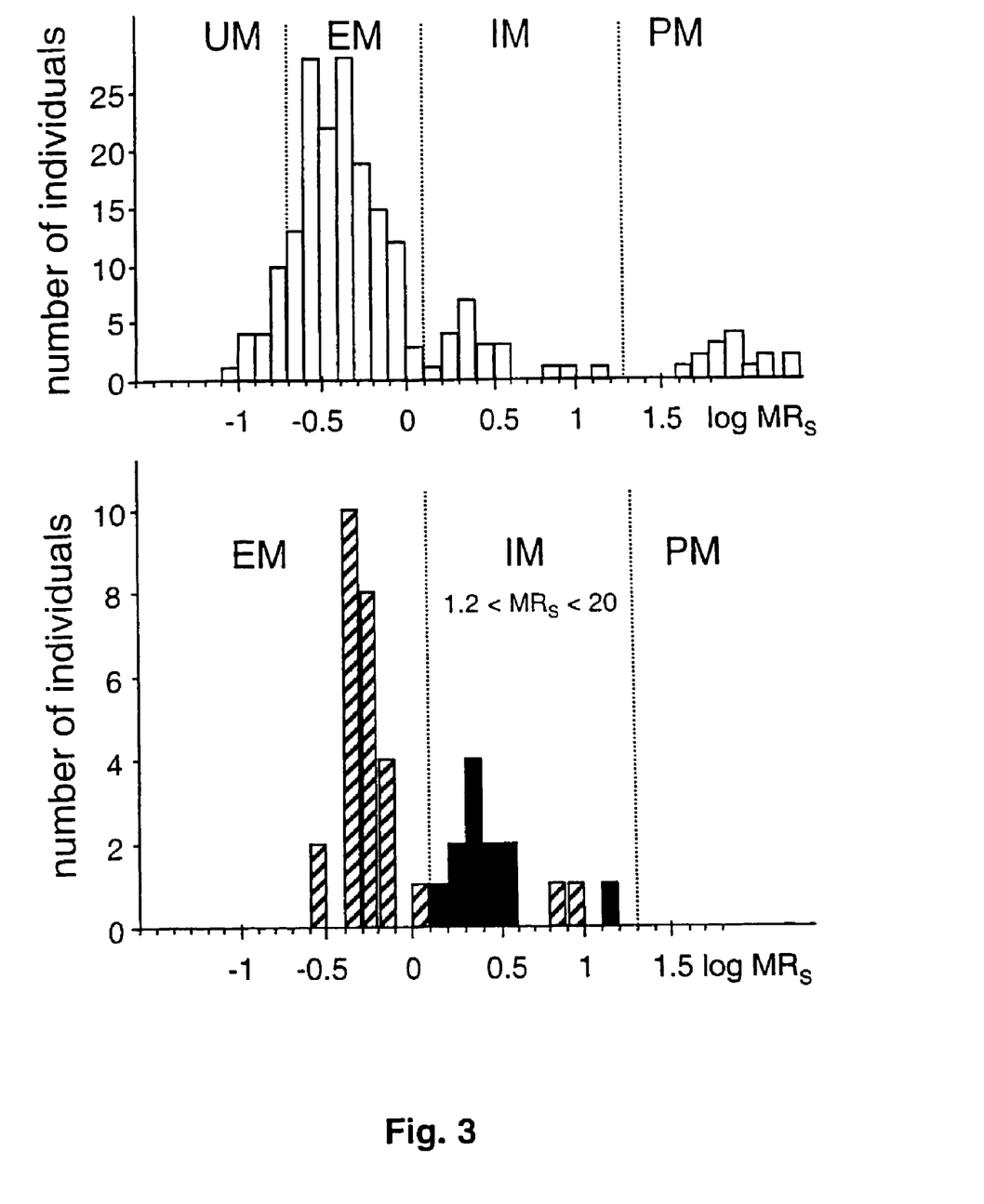
FIG. 3: CYP2D6 phenotype and genotype analysis in Caucasian populations.

Of 39 individuals with genotype CYP2D6*2/*0 (*0 indicating any of the analyzed nonfunctional alleles *3, *4, *5, *6, *7, *8), the median $MR_S$ of individuals with the −1584G promoter variant was 0.53 compared to 2.33 for carriers of *2[−1584C] (FIG. 3; P<0.0001, Mann-Whitney test).

Of the other mutations described in table 2, three functionally neutral mutations were previously described in the CYP2D locus derived from a Chinese individual (Johansson et al., 1994). Two further novel mutations were specifically associated with all *2 alleles sequenced and two further rare mutations were observed (Table 2).

3. Significance of the Findings of the Invention:

The strong association of the common C to G mutation at −1584 bp with increased enzyme activity significantly improves the correlation between genotype and phenotype in the CYP2D6 polymorphism. In particular, this discovery is a strong indication that not only the PM phenotype is genetically inherited but also the sub-phenotype characterized by low enzyme activity. Specifically, testing for the mutation at −1584 bp will allow to identify a large fraction of the "intermediate metabolizers". The analyses show that over 60% of the IMs have the *2/*0 genotype (*0 stands for any nonfunctional allele, i.e. *3, *4, *5, *6, *7, *8 and others). However, this genotype is also common among normal extensive metabolizers and therefore by itself does not allow to predict the IM phenotype. The presence of the wild-type sequence (C) at position −1584 bp is a marker for low activity of the *2/*0 genotype, whereas presence of the mutation (G) is a marker for high activity. Detection of C or G at position −1584 bp in conjunction with identification of the *2/*0 genotype will therefore allow to make a quantitative prediction on the in vivo drug metabolism capacity.

About 10% of the population are phenotypically intermediate metabolizers (Griese et al., 1998). It has been shown that these individuals have a dramatically reduced capacity for clearance of CYP2D6-substrates which is almost as low as that of poor metabolizers. It can be assumed, therefore, that normal doses of drugs that are affected by the CYP2D6 polymorphisms will lead to adverse side effects or therapeutic failure in IMs to an extent comparable to that of PMs. In addition to debrisoquine and sparteine, many other drugs are inefficiently metabolized in PM subjects, including antiarrhythmics, beta adrenergic receptor antagonists, antidepressants, neuroleptics, opioids, amphetamines, and others (Eichelbaum and Gross, 1990; Meyer and Zanger, 1997).

Example 2

CYP2D6 was quantitated immunologically and enzymatically in liver biopsies from 76 individuals with known sparteine oxidation phenotype. All important known alleles including the −1584 C/G promoter polymorphism were determined.

1. Description of Methods:

Patients and Liver Samples. Liver tissue was obtained as wedge biopsy specimens from patients undergoing cholecystectomy between 1983 and 1986 and stored at −80° C. All patients included here had been phenotyped with respect to their sparteine metabolizer phenotype before laparotomy (Osikowska-Evers et al., 1987).

CYP2D6 Genotyping. CYP2D6 alleles were assigned based on the determination of the appropriate key mutations using established PCR assays for alleles *2, *3, *4, *5, *6, *7, *8, *9, and *10 (Stüven et al., 1996; Griese et al., 1998). The C/G mutation was determined using a novel real-time PCR method (Zanger et al., 2001).

Preparation of DNA and of Liver Microsomes. Genomic DNA was isolated from a fraction of liver tissue using the QIAamp Tissue Kit (Qiagen, Hilden, Germany). Microsomes were prepared by standard procedures (Zanger et al., 1988b).

Quantition of CYP2D6 Protein in Liver Microsomes. The monoclonal antibody, Mab 114 (Zanger et al., 1988a) was used for quantitation of CYP2D6 in microsomal fractions by immunoblotting. Bound antibody was detected with the ECL Western Blot Detection System (Amersham Pharmacia Biotech, Freiburg, Germany). Luminescence was analyzed by autoradiography and densitometrical quantitation using an optical scanner (Hirschmann, Neuried, Germany) (Zanger et al., 2001).

Determination of Enzyme Activity. As a specific in vitro enzyme assay for CYP2D6, cumene hydroperoxide-mediated bufuralol 1'-hydroxylation was measured. Assay conditions were similar as described before (Zanger et al., 1988b).

Statistical Methods. Data were analyzed by Kruskal-Wallis non-parametric analysis of variance to establish an overall difference between genotype or phenotype groups. The Student's t-test or the Mann-Whitney U-test was used for pair comparisons, depending on whether the data sets were normally distributed or not, which was tested by the method of Kolmogorov and Smirnov. Means of data are represented with standard deviations (SD), medians with minimal and maximal values observed, and, where indicated, the lower and upper 95% confidence intervals (CI) are given. A P-value of 0.05 or less was considered as significant (n.s., not significant). Statistical calculations were performed using the software GraphPad Instat 3.00 (Graph Pad Inc, San Diego, Calif.).

2. Description of the Results

Figure 4:
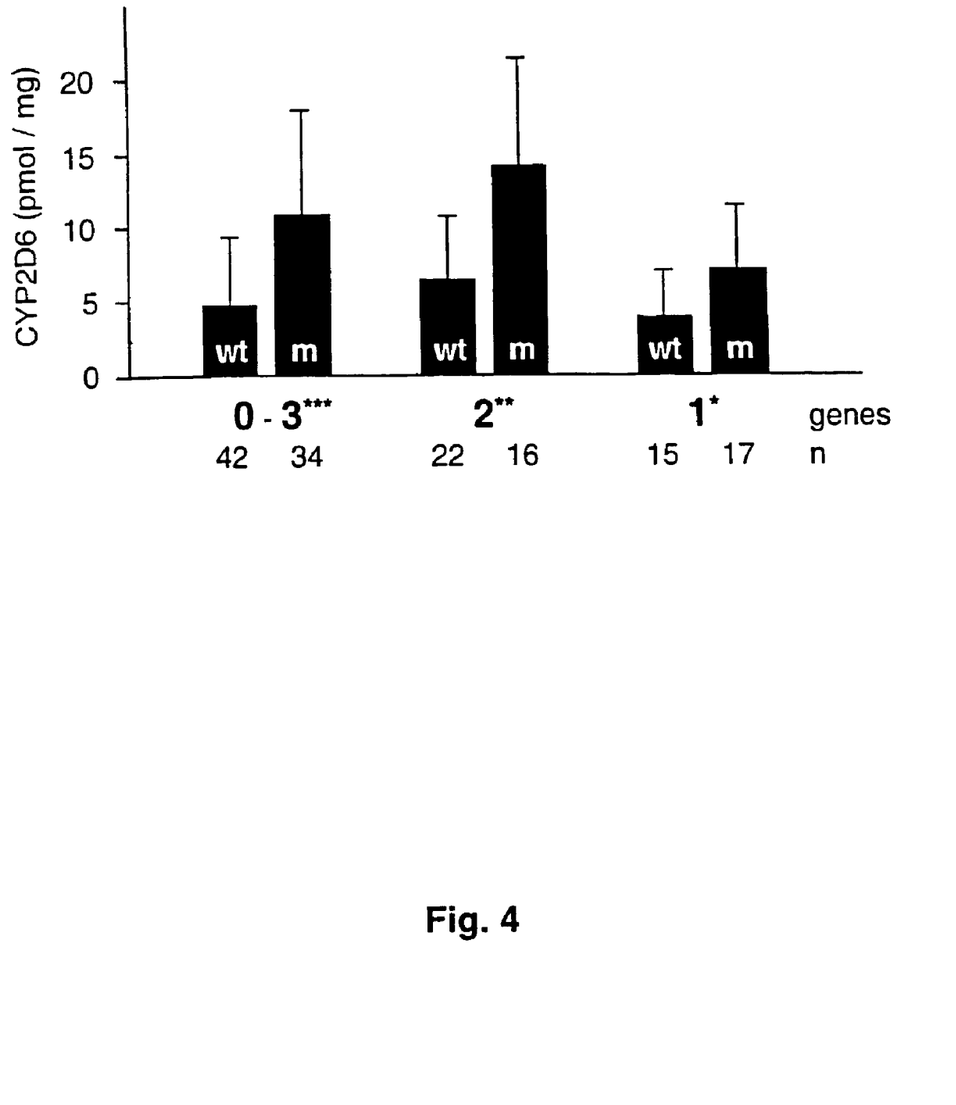
FIG. 4: Microsomal CYP2D6 protein expression in relation to CYP2D6 promoter polymorphism. The promoter genotype at −1584 bp was determined and mean±SD of CYP2D6 protein was calculated for all individuals (0-3 genes) with homozygous wild-type genotype (−1584 CC, "wt") or at least one mutant promoter (−1584 CG or GG, "m") and accordingly for individuals with two or one functional gene copy. Statistical significance: *P=0.026; P=0.001; *P<0.0001 (t-test).

Analysis of the—C/G Promoter Polymorphism. The mutant promoter type G was present in 37 of 152 alleles, corresponding to an overall frequency of 24.3%. It was strongly linked to the *2 allele and only detected once in a sample (*1/*1) that lacked a *2-allele. Irrespective of the genotype or the number of functional alleles, individuals with −1584 C/C promoter type expressed on average less than half CYP2D6 protein (5.5±3.9 pmol/mg, CI 4.2-6.8, 5 poor metabolizers not included) as compared to individuals with −1584 C/G or G/G genotypes (10.9±7.1 pmol/mg, CI 8.4-13.3, P=0.001, U-test). Similar differences were observed between groups with one and two functional alleles (FIG. 4).

CYP2D6 Expression and Phenotype in Relation to Genotype. By taking the −1584 C/G polymorphism into consideration, a total of 19 genotypes could be distinguished in this population sample. To simplify analysis, genotypes involving null-alleles, which do not make a contribution to CYP2D6 expression and in vivo function, were grouped together and collectively termed *0. This analysis revealed that the −1584 G promoter type was consistently associated with higher protein expression and function.

Figure 5:
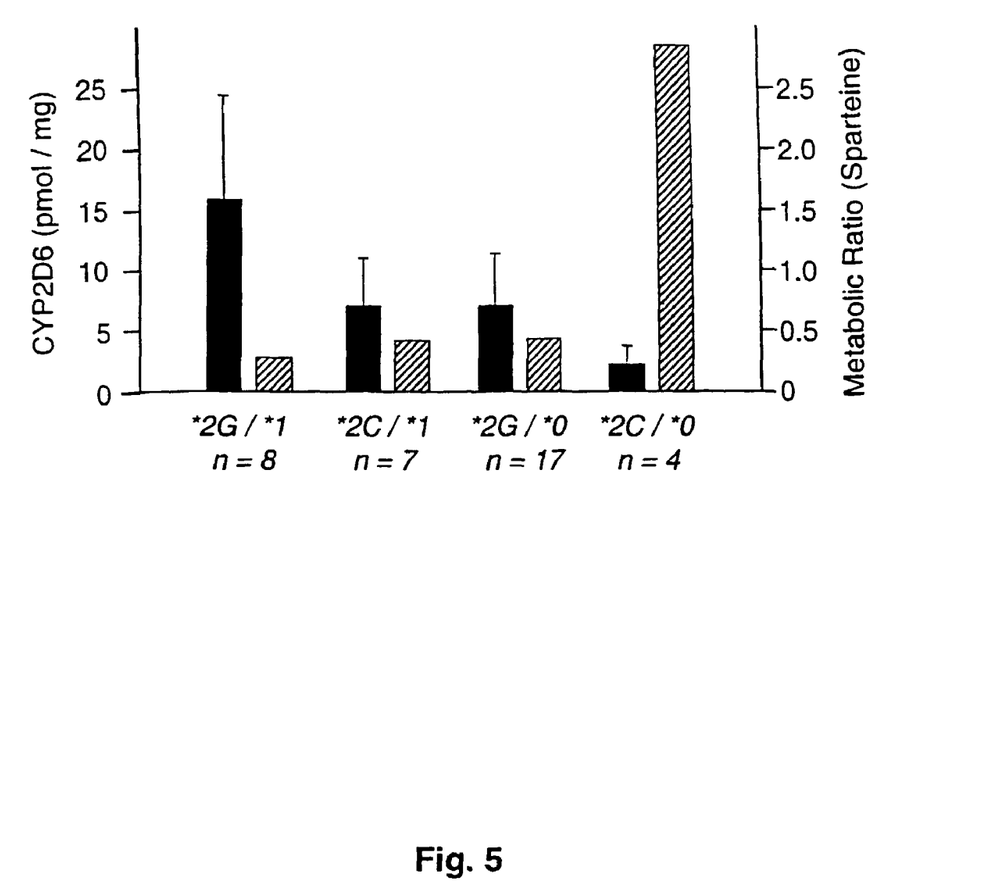
FIG. 5: Relationship between microsomal CYP2D6 protein and in vivo drug oxidation phenotype and CYP2D6 genotypes involving the −1584 C/G promoter mutation. Microsomal CYP2D6 protein content is represented by black bars (left ordinate) and metabolic ratio for sparteine oxidation by hatched bars (right ordinate). The number of individuals in each group is indicated. The difference in protein expression between genotypes *2G/*0 and *2C/*0 was 3.1-fold (7.1±4.4 pmol/mg, CI 4.8-9.1 and 2.3±1.4 pmol/mg, CI 0.01-4.6, respectively; P=0.002, t-test) and 5.6-fold in the in vivo MRs (P<0.001, t-test).

The largest and most significant difference was found between the heterozygous genotypes *2[G]/*0 and *2[C]/*0, due to the absence of confounding functional alleles. The difference in protein expression was 3.1-fold (7.1±4.4 pmol/mg, CI 4.8-9.1 and 2.3±1.4 pmol/mg, CI 0.01-4.6, respectively; P=0.002, t-test) and 5.6-fold in the in vivo MRS (P<0.001, t-test) (FIG. 5). Moreover, genotype *2[C]/*0 was a specific predictor of the IM phenotype and accounted for four of seven IMs in the whole population sample (Table 3), whereas all 17 carriers of the *2[G]/*0 genotype had MRS values <1 and were thus phenotypic EMs. The increase in protein expression associated with the *2[G] allele was strong enough to be even significant on the background of the wild type allele in the mixed genotypes *1/*2[G] and *1/*2[C] (FIG. 4; P=0.026, t-test).

TABLE 3

Phenotypic and genotypic properties of individuals with ultrarapid (UM) and intermediate (IM) metabolizer phenotype.

| individual # | MR (sparteine) | CYP2D6 Genotype | −1584 bp Genotype | CYP2D6 (pmol/mg)[1] |
|---|---|---|---|---|
| Ultrarapid Metabolizers | | | | |
| 24 | 0.07 | *1/*2 × 2 | CG | 24,4 |
| 38 | 0.15 | *2/*2 | GG | 17,9 |
| 58 | 0.17 | *1/*2 | CG | 34,4 |
| 54 | 0.19 | *1/*2 | CG | 18,3 |
| Intermediate Metabolizers | | | | |
| 30 | 1,26 | *1/*4 | CC | 7,94 |
| 21 | 1,90 | *6/*10 | CC | 0,81 |
| 64 | 2,08 | *2/*4 | CC | 2,48 |
| 66 | 2,17 | *2/*4 | CC | 2,87 |
| 75 | 3,03 | *2/*4 | CC | 0,25 |
| 72 | 4,13 | *2/*4 | CC | 3,60 |
| 69 | 6,46 | *1/*1 | CC | 0,50 |

[1]Microsomal CYP2D6 protein content as determined by monoclonal antibody Mab 114.

In the lower MRS range (high activity), there was a striking overrepresentation of the −1584 G promoter type. Up to a MRS of 0.37, all *2-alleles (n=17) were of the −1584 G type, whereas it was not found among individuals with the IM phenotype. Among individuals with UM phenotype, five of eight alleles of the four UM individuals carried the −1584 G mutation.

3. Significance of the Data

These data demonstrated significantly increased protein expression and function in conjunction with the −1584 G promoter type and confirmed the significance of the −1584 C/G promoter polymorphism for CYP2D6 protein expression and the resulting in vivo phenotype. They are in agreement with the assumption of increased gene transcription as a consequence of the alteration of a putative NF-kappa B consensus binding site by mutation −1584 C>G (Raimundo et al., 2000).

REFERENCES

Broly F, Meyer U A (1993) Debrisoquine oxidation polymorphism: phenotypic consequences of a 3-base-pair deletion in exon 5 of the CYP2D6 gene. Pharmacogenetics 3:123-130

Dahl M L, Johansson I, Bertilsson L, Ingelman Sundberg M, Sjoqvist F (1995) Ultrarapid hydroxylation of debrisoquine in a Swedish population. Analysis of the molecular genetic basis. J Pharmacol Exp Ther 274:516-520

Daly A K, Brockmöller J, Broly F, Eichelbaum M, Evans W E, Gonzalez F J, Huang J-D et al (1996) Nomenclature for human CYP2D6 alleles. Pharmacogenetics 6:193-201

Eichelbaum M, Spannbrucker N, Steincke B, Dengler J J (1979) Defective N-oxidation of sparteine in man: a new pharmacogenetic defect. Eur J Clin Pharmacol 16:183-187

Eichelbaum M, Baur M P, Dengler H J, Osikowska Evers B O, Tieves G, Zekorn C, Rittner C (1987) Chromosomal assignment of human cytochrome P-450 (debrisoquine/sparteine type) to chromosome 22. Br. J. Clin. Pharmacol. 23:455-458.

Eichelbaum M, Gross A S (1990) The genetic polymorphism of debrisoquine/sparteine metabolism-clinical aspects. Pharmacol Ther 46:377-394

Griese U, Zanger U M, Brudermanns U, Gaedigk A, Mikus G, Mörike K, Stüven T, Eichelbaum M (1998) Assessment of the predictive power of genotypes for the in-vivo catalytic function of CYP2D6 in a German population. Pharmacogenetics 8:15-26

Hardman J G, Gilman, Limbird L E (ed) (1995) Goodman & Gilman's The Pharmacological Basis of Therapeutics. Ninth Edition McGraw-Hill Johansson I, Oscarson M, Yue Q Y, Bertilsson L, Sjoqvist F, Ingelman-Sundberg M (1994) Genetic analysis of the Chinese cytochrome P4502D locus: characterization of variant CYP2D6 genes present in subjects with diminished capacity for debrisoquine hydroxylation. Mol Pharmacol. 46:452-459.

Johansson I, Lundqvist E, Bertilsson L, Dahl M L, Sjoqvist F, Ingelman Sundberg M (1993) Inherited amplification of an active gene in the cytochrome P450 CYP2D locus as a cause of ultrarapid metabolism of debrisoquine. Proc Natl Acad Sci USA 90:11825-11829

Kimura S, Umeno M, Skoda R C, Meyer U A, Gonzalez F J (1989) The human debrisoquine 4-hydroxylase (CYP2D) locus: sequence and identification of the polymorphic CYP2D6 gene, a related gene, and a pseudogene. Am J Hum Genet 45:889-904

Mahgoub A, Idle J R, Dring L G, Lancester R, Smith R L (1977) Polymorphic hydroxylation of debrisoquine in man. Lancet ii:584-586

Marshall A (1997a) Laying the foundations for personalized medicines. Nat Biotechnol 15:954-957

Marshall A (1997b) Getting the right drug into the right patient. Nat Biotechnol 15:1249-1252

Marez D, Legrand M, Sabbagh N, Lo Guidice J-M, Spire C, Lafitte J-J, Meyer U A et al (1997) Polymorphism of the cytochrome P450 CYP2D6 gene in a European population: Characterization of 48 mutations and 53 alleles, their frequencies and evolution. Pharmacogenetics 7:193-202

Meyer U A, Zanger U M (1997) Molecular mechanisms of genetic polymorphisms of drug metabolism. Annu Rev Pharmacol Toxicol 37:269-296

Osikowska-Evers B, Dayer P, Meyer U A, Robertz G M, Eichelbaum M. Evidence for altered catalytic properties of the cytochrome P450 involved in sparteine oxidation in poor metabolizers. Clin Pharmacol Ther 1987; 41:320-325.

Raimundo S, Fischer J, Eichelbaum M, Griese E U, Schwab M, Zanger U M. Elucidation of the genetic basis of the common 'intermediate metabolizer' phenotype for drug oxidation by CYP2D6. Pharmacogenetics 2000; 10:577-581.

Sachse C, Brockmöller J, Bauer S, Roots I (1997) Cytochrome P450 2D6 variants in a Caucasian population: allele frequencies and phenotypic consequences. Am J Hum Genet 60:284-295

Stüven T, Griese E U, Kroemer H K, Eichelbaum M, Zanger U M (1996). Rapid detection of CYP2D6 null-alleles by long distance and multiplex polymerase chain reaction. Pharmacogenetics 6:417-421.

West W L, Knight E M, Pradhan S, Hinds T S (1997) Inter-patient variability: genetic predisposition and other genetic factors. J Clin Pharmacol. 37:635-48.

Yokota H, Tamura S, Furuya H, Kimura S, Watanabe M, Kanazawa I, Kondo I et al (1993) Evidence for a new variant CYP2D6 allele CYP2D6J in a Japanese population associated with lower in vivo rates of sparteine metabolism. Pharmacogenetics 3:256-263

Zanger U M, Hauri H P, Loeper J, Homberg J C, Meyer U A. Antibodies against human cytochrome P-450db1 in autoimmune hepatitis type II. Proc Natl Acad Sci USA 1988a; 85:8256-8260.

Zanger U M, Vilbois F, Hardwick J P, Meyer U A. Absence of hepatic cytochrome P450bufI causes genetically deficient debrisoquine oxidation in man. Biochemistry 1988b; 27:5447-5454.

Zanger U M. Immunoisolation of human microsomal cytochromes P450 using autoantibodies. Methods Enzymol 1991; 206:201-209.

Zanger U M, Fischer J, Raimundo S, Stüven T, Evert B O, Schwab M, Eichelbaum M. Comprehensive Analysis of the Genetic Factors Determining Expression and Function of Hepatic CYP2D6. Pharmacogenetics 2001 (in press).

The invention claimed is:

1. A method of identifying a human subject as being at risk for reduced CYP2D6 activity, comprising:
   (a) detecting in vitro in a sample from the human subject the CYP2D6 genotype at position 36 of SEQ ID NO: 1; and
   (b) identifying the human subject having a homozygous Cytosine (C) at position 36 of SEQ ID NO: 1 as having risk for reduced CYP2D6 activity relative to a human subject having a heterozygous or homozygous Guanine (G) at position 36 of SEQ ID NO: 1.

2. The method of claim 1 wherein detection is performed using at least one of polymerase chain reaction (PCR), ligase chain reaction, restriction digestion, direct sequencing, nucleic acid amplification techniques and hybridization techniques.

3. The method of claim 1, wherein the detecting step utilizes polymerase chain reaction (PCR).

4. The method of claim 1, wherein the detecting step utilizes a nucleic acid molecule of 15-50 nucleotides that hybridizes to a polynucleotide comprising a C at position 36 of SEQ ID NO: 1.

5. The method of claim 3, wherein the PCR product comprises a C at position 36 of SEQ ID NO: 1.

6. A method of identifying a human subject as being at risk for reduced CYP2D6 activity, comprising:
   (a) detecting in vitro in a sample from the human subject the nucleotide at polymorphic site −1584 of the CYP2D6 gene promoter, which is position 36 of SEQ ID NO: 1, and
   (b) identifying the human subject having a homozygous Cytosine (C) at said polymorphic site -1584 of the CYP2D6 gene promoter as having risk for reduced CYP2D6 activity relative to a human subject having a heterozygous or homozygous Guanine (G) at said polymorphic site.

7. The method of claim 6, wherein detection is performed using at least one of polymerase chain reaction (PCR), ligase chain reaction, restriction digestion, direct sequencing, nucleic acid amplification techniques and hybridization techniques.

8. The method of claim 6, wherein the detecting step utilizes polymerase chain reaction (PCR).

9. The method of claim 6, wherein the detecting step utilizes a nucleic acid molecule of 15-50 nucleotides that hybridizes to a polynucleotide comprising a C at position 36 of SEQ ID NO: 1.

10. The method of claim 8, wherein the PCR product comprises a C at position 36 of SEQ ID NO: 1 or the complement thereof.

* * * * *

UNITED STATES PATENT AND TRADEMARK OFFICE
CERTIFICATE OF CORRECTION

| | | |
|---|---|---|
| PATENT NO. | : 8,129,112 B2 | Page 1 of 1 |
| APPLICATION NO. | : 10/182977 | |
| DATED | : March 6, 2012 | |
| INVENTOR(S) | : Sebastian Raimundo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
Twenty-fourth Day of July, 2012

David J. Kappos
*Director of the United States Patent and Trademark Office*

SEQUENCE LISTING

```
<160> NUMBER OF SEQ ID NOS: 12

<210> SEQ ID NO 1
<211> LENGTH: 1669
<212> TYPE: DNA
<213> ORGANISM: Homo sapiens

<400> SEQUENCE: 1
gaattcaaga ccagcctgga caacttggaa gaaccsggtc tctacaaaaa atacaaaatt      60
agctgggatt gggtgcggtg gctcatgcct ataatcccag cactttggga gcctgaggtg     120
ggtggatcac ctgaagtcag gagttcaaga ctagcctggc caacatggtg aaaccctatc     180
tctactgaaa atayaaaaag ctagacgtgg tggcacacac ctgtaatccc agctacttag     240
gaggctgagg caggagaatt gcttgaagcc tagaggtgaa ggttgtagtg agccgagatt     300
gcatcattgc acaatggagg ggagccacca gcctgggcaa caagaggaaa tctccgtctc     360
caaaaaaaaa aaaaaaaaaa aaagrattag gctgggtggt gcctgtagtc ccagctactt     420
gggaggcagg gggtccactt gatgtcgaga ctgcagtgag ccatgatcct gccactgcac     480
tccggcctgg gcaacagagt gagaccctgt ctaaagaaaa aaaaaataaa gcaacatatc     540
ctgaacaaag gatcctccat aacgttccca ccagatttct aatcagaaac atggaggcca     600
gaaagcagtg gaggaggacr accctcaggc agcccggag gatgttgtca caggctgggg     660
caagggcctt ccggctacca actgggagct ctgggaacag ccctgttgca aacaagaagc     720 catgcccgg ccagagccca ggaatgtggg ctgggctggg agcagcctct ggacaggagt     780
ggtcccatcc aggaaacctc cggcatggct gggaagtggg gtacttggtg ccgggtctgt     840
atgtgtgtgt gactggtgtg tgtgagagag aatgtgtgcy ctaagtgtca gtgtgagtct     900
gtgtatgtgt gaatattgtc tttgtgtggg tgatttctr cgtgtgtaat cgtgtccctg     960
caagtgtgaa caagtggaca agtgtctggg agtggacaag agatctgtgc accatcaggt    1020
gtgtgcatag cgtctgtgca tgtcaagagt gcaaggtgaa gtgaagggac caggcccatg    1080
atgccactca tcatcaggag ctctaaggcc ccaggtaagt gccagtgaca gataagggtg    1140
ctgaaggtca ctctggagtg ggcaggtggg ggtagggaaa gggcaaggcc atgttctgga    1200
ggaggggttg tgactacatt agggtgtatg agcctagctg ggaggtggat ggccrggtcc    1260
actgaaaccc tggttatccc agaaggcttt gcaggctyca ggagcttgga gtggggagag    1320
ggggtgactt ctccgaccag gcccctccac cggcctaccc tgggtaaggg cctggagcag    1380
gaagcagggg caagaacctc tggagcagcc catacccgcc ctggcctgac tctgccactg    1440
gcagcacagt caacacagca ggttcactca cagcagaggg caaaggccat catcagctcc    1500
```

-continued

```
ctttataagg gaagggtcac gcgctcggtg tgctgagagt gtcctgcctg gtcctctgtg    1560
cctggtgggg tggggtgcc aggtgtgtcc agaggagccc atttggtagt gaggcaggta    1620
tggggctaga agcactggtg cccctggccg tgatagtggc catcttcct              1669
```

```
<210> SEQ ID NO 2
<211> LENGTH: 22
<212> TYPE: DNA
<213> ORGANISM: Artificial sequence
<220> FEATURE:
<223> OTHER INFORMATION: Synthetic sequence designed from genomic DNA

<400> SEQUENCE: 2
gcctggacaa cttggaagaa cc                                              22

<210> SEQ ID NO 3
<211> LENGTH: 20
<212> TYPE: DNA
<213> ORGANISM: Artificial sequence
<220> FEATURE:
<223> OTHER INFORMATION: Synthetic sequence designed from genomic DNA

<400> SEQUENCE: 3
aggaagatgg ccactatcac                                                 20

<210> SEQ ID NO 4
<211> LENGTH: 21
<212> TYPE: DNA
<213> ORGANISM: Artificial sequence
<220> FEATURE:
<223> OTHER INFORMATION: Synthetic sequence designed from genomic DNA

<400> SEQUENCE: 4
gaacaagtgg acaagtgtct g                                               21

<210> SEQ ID NO 5
<211> LENGTH: 19
<212> TYPE: DNA
<213> ORGANISM: Artificial sequence
<220> FEATURE:
<223> OTHER INFORMATION: Synthetic sequence designed from genomic DNA

<400> SEQUENCE: 5
ccatacctgc ctcactacc                                                  19

<210> SEQ ID NO 6
<211> LENGTH: 22
<212> TYPE: DNA
<213> ORGANISM: Artificial sequence
<220> FEATURE:
<223> OTHER INFORMATION: Synthetic sequence designed from genomic DNA

<400> SEQUENCE: 6
ttcccaccag atttctaatc ag                                              22

<210> SEQ ID NO 7
<211> LENGTH: 20
<212> TYPE: DNA
<213> ORGANISM: Artificial sequence
<220> FEATURE:
<223> OTHER INFORMATION: Synthetic sequence designed from genomic DNA

<400> SEQUENCE: 7
cagcaccctt atctgtcact                                                 20

<210> SEQ ID NO 8
```

```
<211> LENGTH: 19
<212> TYPE: DNA
<213> ORGANISM: Artificial sequence
<220> FEATURE:
<223> OTHER INFORMATION: Synthetic sequence designed from genomic DNA

<400> SEQUENCE: 8
gtcctcctcc actgctttc                                                    19

<210> SEQ ID NO 9
<211> LENGTH: 23
<212> TYPE: DNA
<213> ORGANISM: Artificial sequence
<220> FEATURE:
<223> OTHER INFORMATION: Synthetic sequence designed from genomic DNA

<400> SEQUENCE: 9
ttagacaggg tctcactctg ttg                                               23

<210> SEQ ID NO 10
<211> LENGTH: 22
<212> TYPE: DNA
<213> ORGANISM: Artificial sequence
<220> FEATURE:
<223> OTHER INFORMATION: Synthetic sequence designed from genomic DNA

<400> SEQUENCE: 10
gacggagatt tcctcttgtt gc                                                22

<210> SEQ ID NO 11
<211> LENGTH: 13
<212> TYPE: DNA
<213> ORGANISM: Homo sapiens

<400> SEQUENCE: 11
tgggccagag atg                                                          13

<210> SEQ ID NO 12
<211> LENGTH: 13
<212> TYPE: DNA
<213> ORGANISM: Homo sapiens

<400> SEQUENCE: 12
tggcccagag atg                                                          13
```